(12) United States Patent
Morgan et al.

(10) Patent No.: US 10,154,893 B2
(45) Date of Patent: Dec. 18, 2018

(54) RAPID EXCHANGE VENA CAVA FILTER CATHETER AND METHOD OF USE

(71) Applicant: BIO2 MEDICAL, INC., Golden, CO (US)

(72) Inventors: Jeremy Morgan, Idaho Springs, CO (US); Jeffrey N. Steinmetz, Arvada, CO (US); Daniel D. Sims, Arvada, CO (US); Rogelio Guerra, Denver, CO (US); Elijah Atkinson, Arvada, CO (US)

(73) Assignee: Bio2 Medical, Inc., Golden, CO (US)

( * ) Notice: Subject to any disclaimer, the term of this patent is extended or adjusted under 35 U.S.C. 154(b) by 484 days.

(21) Appl. No.: 14/856,521

(22) Filed: Sep. 16, 2015

(65) Prior Publication Data

US 2016/0220345 A1 Aug. 4, 2016

Related U.S. Application Data

(60) Provisional application No. 62/051,153, filed on Sep. 16, 2014.

(51) Int. Cl.
*A61F 2/01* (2006.01)

(52) U.S. Cl.
CPC .......... *A61F 2/013* (2013.01); *A61F 2/01* (2013.01); *A61F 2002/011* (2013.01); *A61F 2002/015* (2013.01); *A61F 2002/016* (2013.01); *A61F 2230/0067* (2013.01); *A61F 2250/0069* (2013.01)

(58) Field of Classification Search
CPC .......... A61F 2002/011; A61F 2002/015; A61F 2002/016; A61F 2/01
See application file for complete search history.

(56) References Cited

U.S. PATENT DOCUMENTS

| | | | |
|---|---|---|---|
| 5,324,259 A | 6/1994 | Taylor et al. | 604/96 |
| 5,395,353 A | 3/1995 | Scribner | 604/264 |
| 5,413,559 A | 5/1995 | Sirhan et al. | 604/102 |
| 5,468,225 A | 11/1995 | Teirstein | 604/102 |
| 5,647,847 A | 7/1997 | Lafontaine et al. | 604/96 |
| 5,728,064 A | 3/1998 | Burns et al. | 604/96 |
| 6,346,093 B1 * | 2/2002 | Allman | A61M 25/0075 604/164.03 |
| 6,613,075 B1 | 9/2003 | Healy et al. | 623/1.11 |
| 6,723,071 B2 | 4/2004 | Gerdts et al. | 604/103.04 |
| 6,730,107 B2 | 5/2004 | Kelly et al. | 606/192 |

(Continued)

FOREIGN PATENT DOCUMENTS

| | | | |
|---|---|---|---|
| JP | 2010-099215 | 5/2010 | A61B 17/10 |
| WO | WO 00/69499 | 11/2000 | A61M 25/01 |

(Continued)

OTHER PUBLICATIONS

Decousus, Herve, et al., "A Clinical Trial of Vena Caval Silters in the Prevention of Pulmonary Embolism in Patients with Proximal Deep-Vein Thrombisis", *The New England Journal of Medicine*, vol. 338, No. 7, pp. 409-415 (Feb. 12, 1998).

(Continued)

*Primary Examiner* — Kathleen Holwerda
*Assistant Examiner* — Sarah Simpson
(74) *Attorney, Agent, or Firm* — David G. Rosenbaum; Benjamin D. Rotman; Rosenbaum IP, P.C.

(57) ABSTRACT

A rapid exchange catheter having a vena cava filter and a method for percutaneous delivery of the rapid exchange vena cava filter for use in indicated medical situations in which prophylactic or therapeutic protection against pulmonary embolism are indicated.

10 Claims, 11 Drawing Sheets

(56) References Cited

U.S. PATENT DOCUMENTS

| | | | | |
|---|---|---|---|---|
| 6,997,908 | B2 | 2/2006 | Carrillo, Jr. et al. | 604/167.06 |
| 7,867,246 | B2 * | 1/2011 | Kim | A61F 2/013 606/200 |
| 8,414,527 | B2 | 4/2013 | Mallaby | 604/103.04 |
| 8,613,753 | B2 | 12/2013 | Angel et al. | 606/200 |
| 8,632,491 | B2 | 1/2014 | Webler et al. | 604/99.03 |
| 8,636,714 | B2 | 1/2014 | McFerran | 604/523 |
| 8,668,712 | B2 | 3/2014 | Angel | 606/200 |
| 8,758,325 | B2 | 6/2014 | Webster et al. | 604/510 |
| 8,771,226 | B2 | 7/2014 | Castella et al. | 604/105 |
| 8,777,977 | B2 | 7/2014 | Angel | 606/200 |
| 8,777,981 | B2 | 7/2014 | Angel | 606/200 |
| 8,784,360 | B2 | 7/2014 | Nelson | 604/30 |
| 8,808,323 | B2 | 8/2014 | Angel et al. | 606/200 |
| 2007/0250106 | A1 | 10/2007 | Kim | 606/200 |
| 2014/0142427 | A1 | 5/2014 | Petroff | 600/427 |
| 2014/0276043 | A1 | 9/2014 | Gupta et al. | 604/434 |
| 2014/0309536 | A1 * | 10/2014 | Douk | A61M 25/003 600/478 |

FOREIGN PATENT DOCUMENTS

| | | | | |
|---|---|---|---|---|
| WO | WO 2002/055146 | 7/2002 | | A61M 29/00 |
| WO | WO 2003/02033 | 1/2003 | | A61F 2/06 |
| WO | WO 2003/068106 | 8/2003 | | A61F 2/01 |
| WO | 2006/105064 | 10/2006 | | G05B 19/418 |
| WO | WO 2011/148626 | 12/2011 | | A61B 17/00 |
| WO | WO 2012/094195 | 7/2012 | | A61M 29/00 |
| WO | WO 2013/052661 | 4/2013 | | A61M 39/06 |

OTHER PUBLICATIONS

Lin, Peter H., et al., "Vena Caval Filters in the Treatment of Acute DVT", *Endovascular Today*, pp. 40-50 (Jan. 2005).

PCT International Search Report issued in a corresponding foreign application, pp. 1-4 (dated Dec. 22, 2015).

PCT Preliminary Report on Patentability issued in a corresponding foreign application, PCT/US2015/050527, pp. 1-6 (dated Mar. 30, 2017).

EP Extended Search Report and Search Opinion; EP 15841628.9, pp. 1-7 (dated May 11, 2018).

* cited by examiner

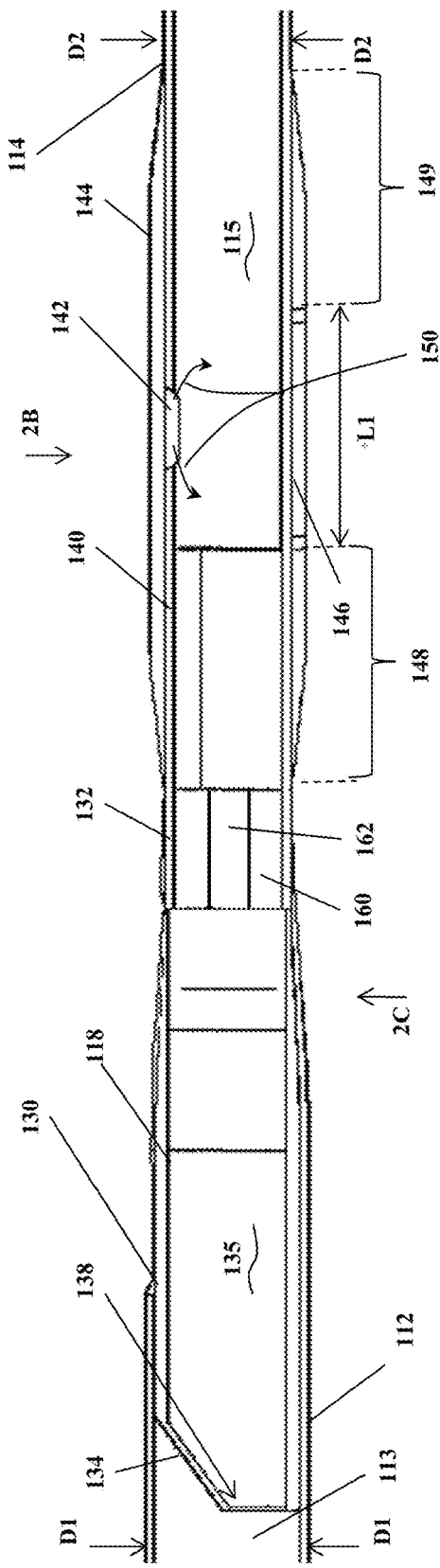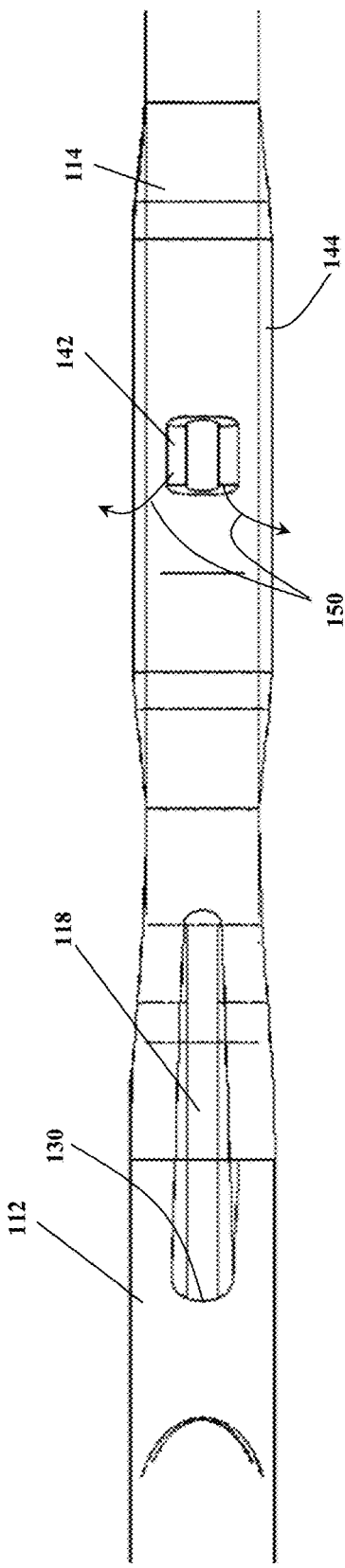
FIG. 2A
FIG. 2B

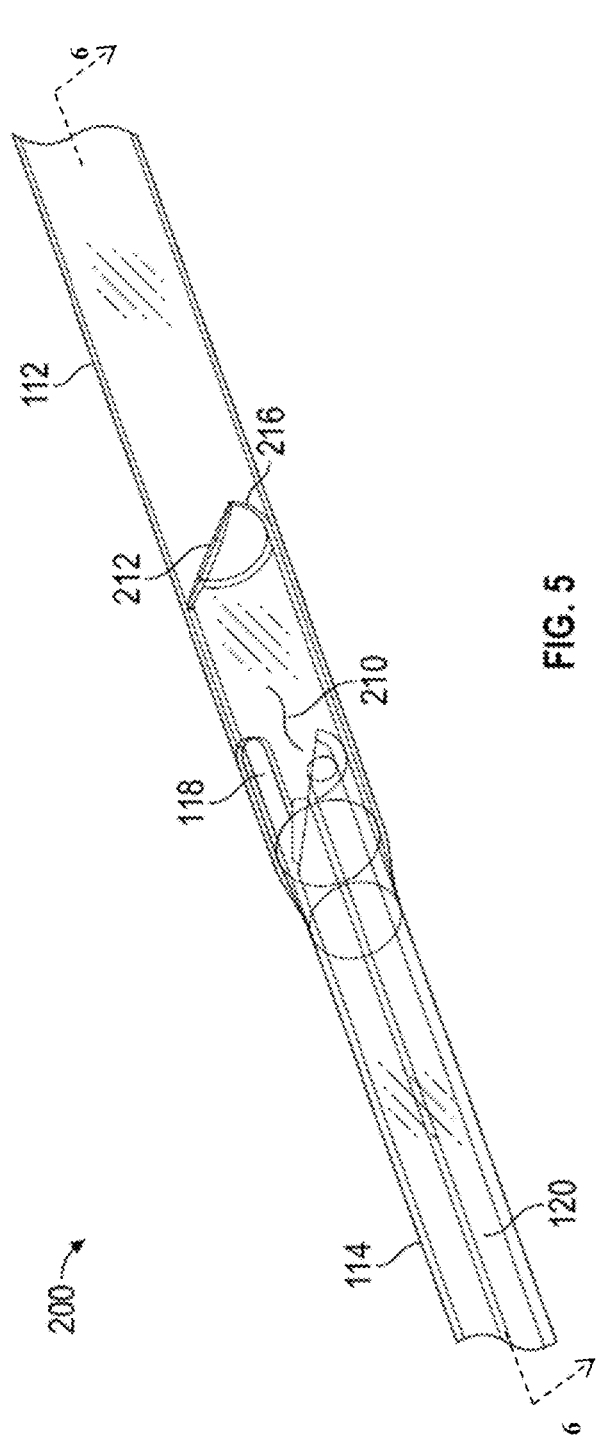
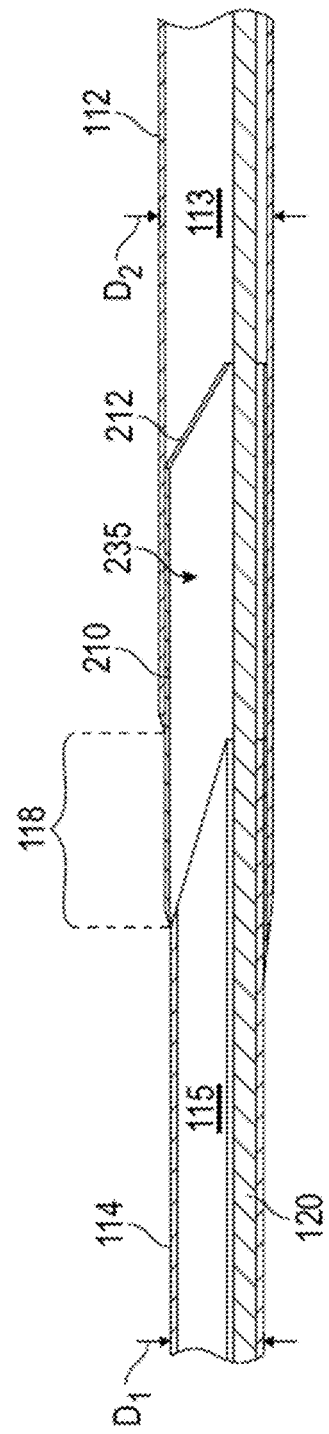
FIG. 5
FIG. 6

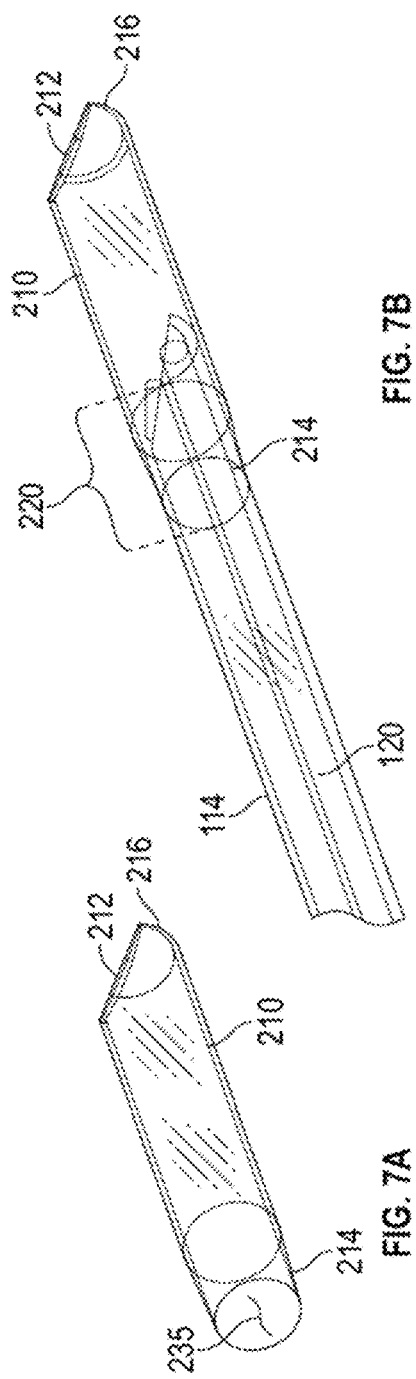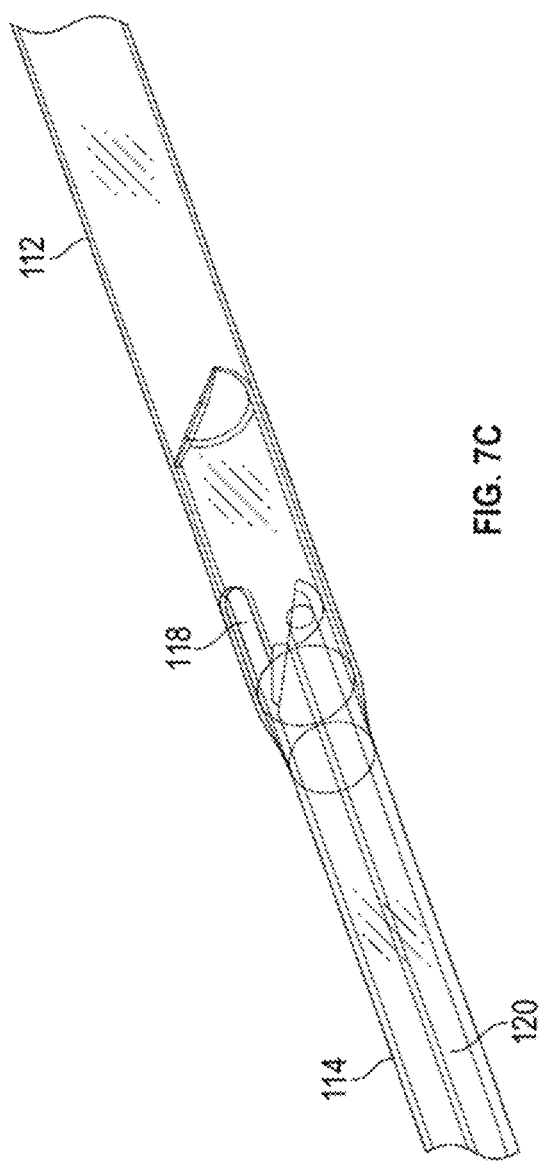

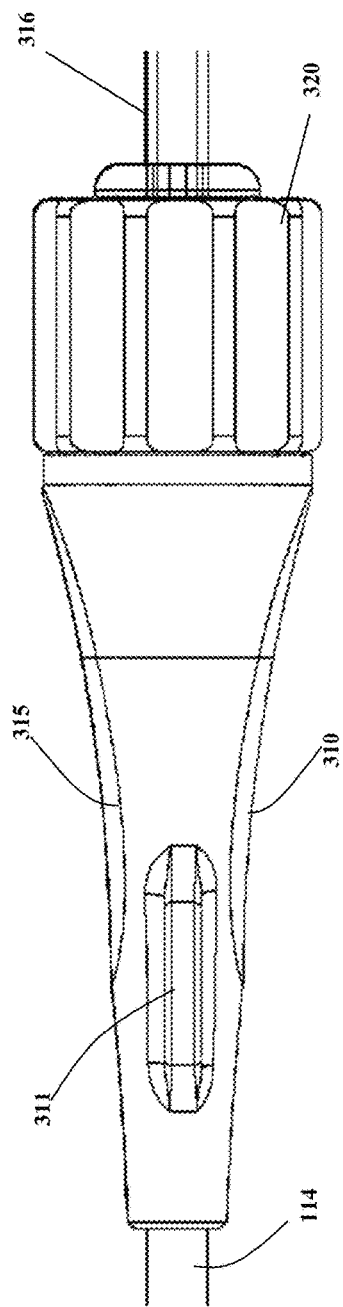
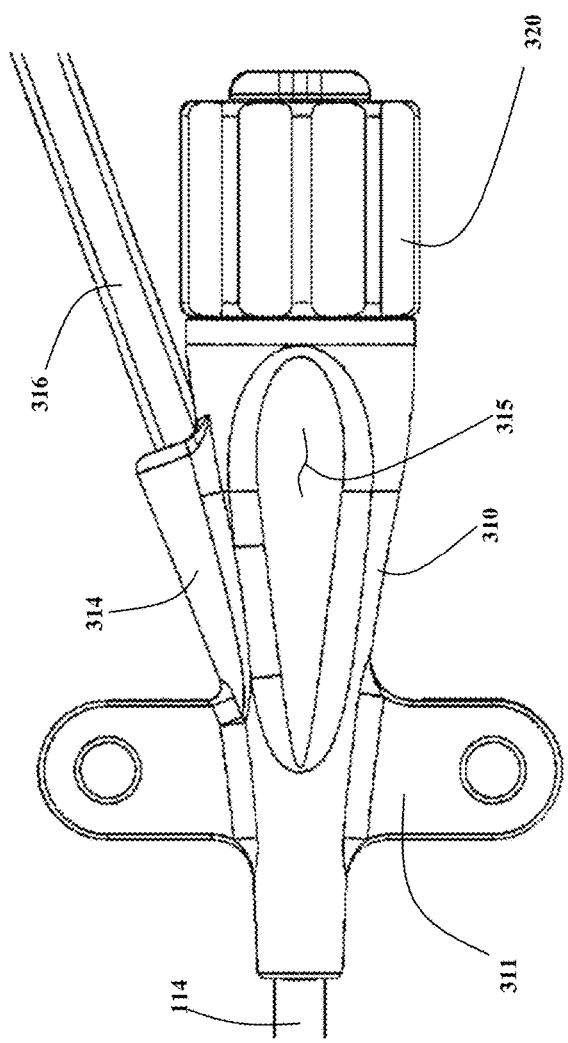
FIG. 9A
FIG. 9B

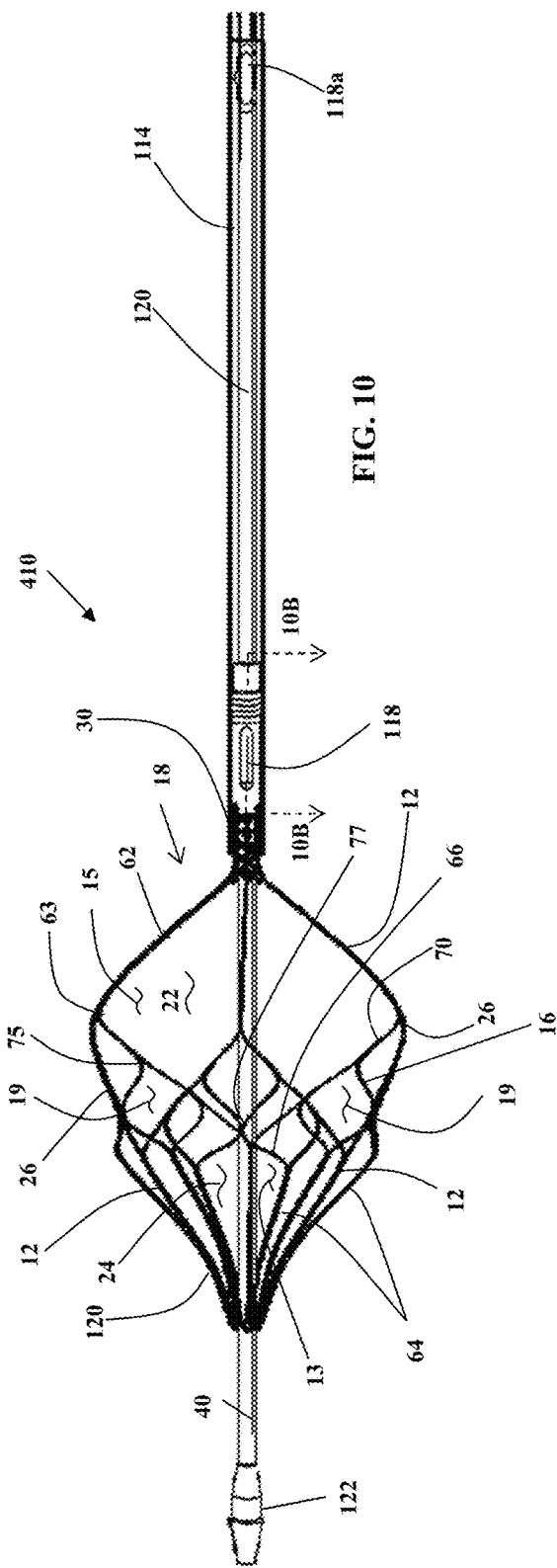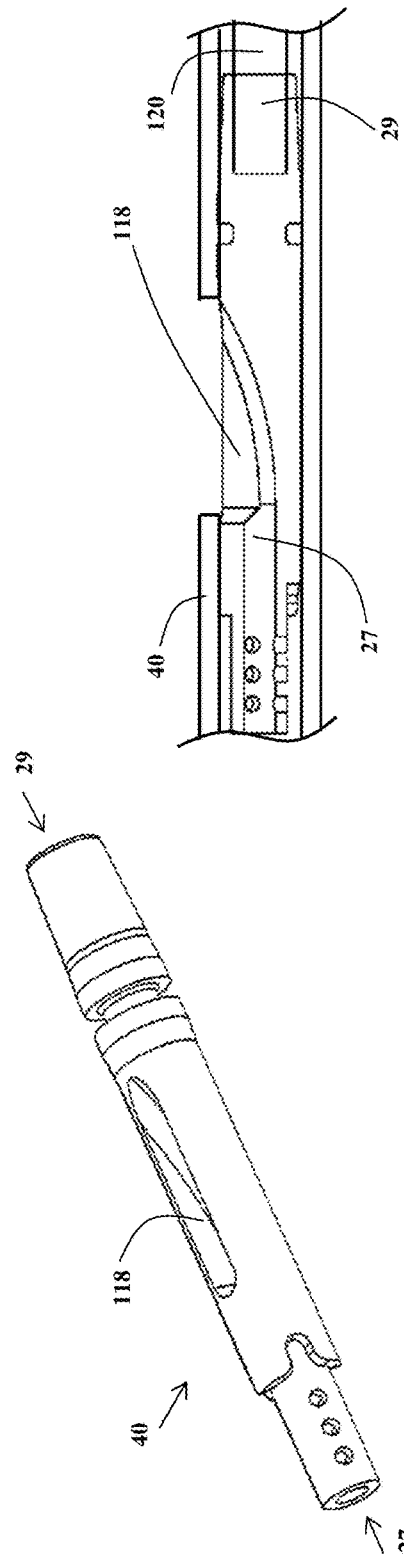
FIG. 10
FIG. 10A
FIG. 10B

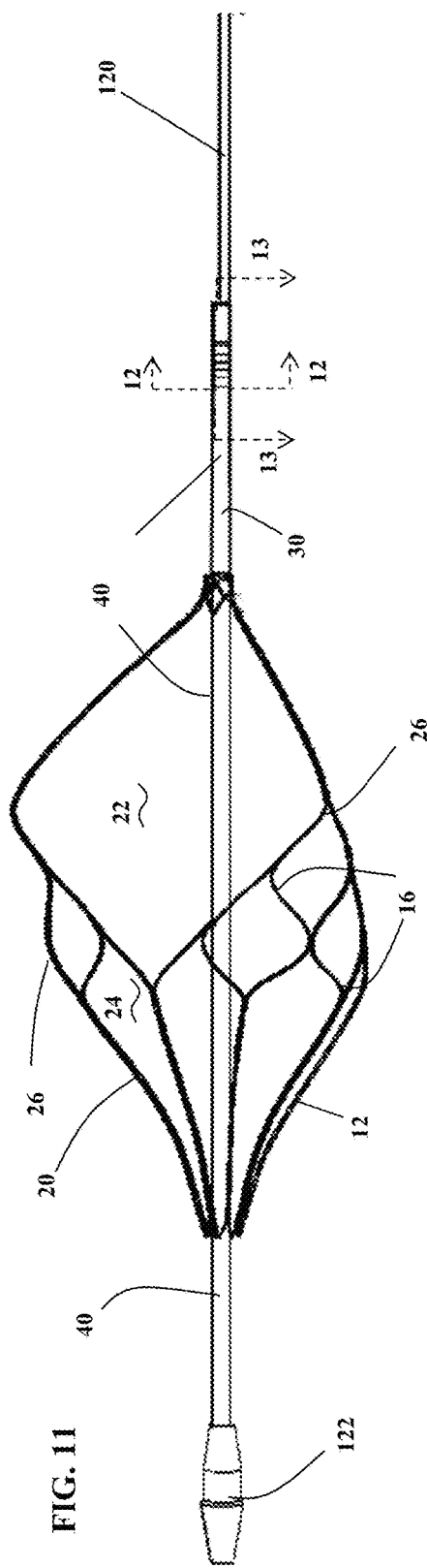
FIG. 11
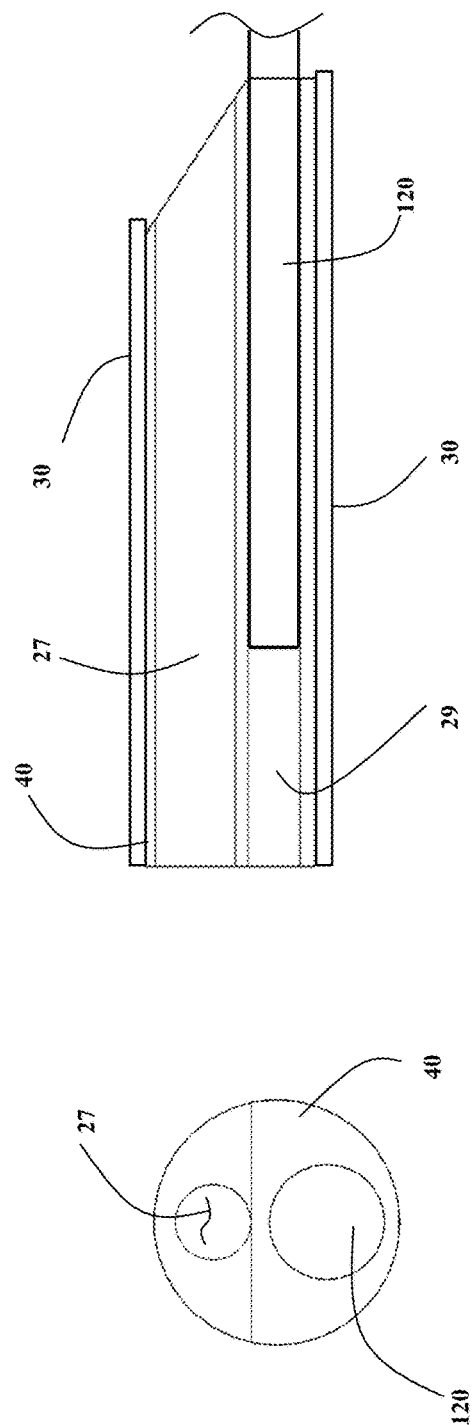
FIG. 12
FIG. 13

RAPID EXCHANGE VENA CAVA FILTER CATHETER AND METHOD OF USE

CROSS-REFERENCE TO RELATED APPLICATIONS

The present application claims priority from U.S. Provisional Application Ser. No. 62/051,153, filed Sep. 16, 2014, herein incorporated by reference in its entirety.

BACKGROUND OF THE INVENTION

The present invention pertains generally to medical catheters and methods of percutaneous delivery of a catheter to a site within the body for diagnostic or therapeutic purposes. More particularly, the present invention relates to a rapid exchange catheter having a tethered or fixedly attached vena cava filter and a method for percutaneous delivery of the rapid exchange vena cava filter for use in indicated medical situations in which prophylactic or therapeutic protection against pulmonary embolism are indicated.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems. Percutaneous delivery through a 6 Fr introducer minimizes the likelihood that surgical intervention to close the access site will be required when the system is withdrawn from the patient.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. *N Engl J Med* 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion.

Currently, there are several different types of U.S. Food and Drug Administration ("FDA") approved vena cava filters. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Günther Tulip filter (Cook Inc.).

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters that are currently available in the United States include the Günther Tulip (Cook Inc.), Opt Ease (Cordis Corp.), and Recovery nitinol filters (Bard Peripheral Vascular, Tempe, Ariz.) Lin P H, et al., Vena caval filters in the treatment of acute DVT. *Endovascular Today* 2005; January: 40-50. The time limit of retrievability is in part dependent on the rate of endothelialization of the device, which typically occurs within 2 weeks, but may occur within five days or as much as 30 days. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement.

SUMMARY OF THE INVENTION

The present invention relates to a central access catheter having a vena cava filter at a distal end, a port proximal the filter and a port distal the filter and plural infusion ports. Accordingly, it is an objective of the present invention to provide a rapid exchange catheter coupled to a vena cava filter that is useful both as a central venous access catheter for administration of intravenous fluids, bioactive agents, contrast agents, flushing agents, pressurized fluids for mechanical thrombolysis and/or withdrawal of blood samples and for capture of thrombus or emboli.

Another aspect of the present invention is to provide a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member.

Yet another aspect of the present invention is to provide an asymmetrical vena cava filter in which the vena cava filter has a distal end that is asymmetrical relative to a proximal end of the filter. In accordance with this aspect of the invention, the vena cava filter includes a first conical section and a second conical section, with each of the first and second conical sections forming one of the proximal end or distal end of the filter. Each of the first and second conical sections taper long the longitudinal axis of the catheter member such that an apex of each conical section is generally co-axial with the longitudinal axis of the catheter member and the catheter member passes through a central longitudinal axis, and both apices of the first and second conical sections, respectively.

It is yet another aspect of the invention to provide a rapid exchange vena cava filter catheter in which a proximal aspect of the catheter has a first diameter and a distal aspect of the catheter has a second larger diameter than the proximal aspect of the catheter.

It is still yet another aspect of the invention to provide a rapid exchange vena cava filter catheter having a rapid exchange guide wire port passing through the distal aspect of the catheter. The rapid exchange guide wire port further includes a seal that permits a guide wire to be passed into and through a central lumen of the catheter, and exit through the rapid exchange guide wire port, while the seal substantially seals the rapid exchange guide wire port such that medically significant fluid flow does not pass through the rapid exchange guide wire port during use within the body.

Still another objective of the present invention is to provide a contrast port medial along a length of the rapid exchange vena cava filter catheter. The contrast port is positioned in a medial position along the length of the rapid exchange vena cava filter catheter in order to allow for sufficient distance between the contrast port and the vena cava filter member for dispersion of a contrast medium within the blood flow to optimize visualization of the vena cava filter member, any region proximal to the filter member, and any thrombus captured by the vena cava filter member.

A further object of the present invention is to configure the medial contrast port such that a flow of contrast agent out of the contrast port occurs only when the contrast agent is introduced at or above a predetermine pressure, while allowing other fluids introduced below such threshold predetermined pressure to pass through the central lumen of the catheter system and bypass the contrast port.

These and other objects, features and advantages of the present invention will be more apparent to those skilled in the art from the following more detailed description of the invention with reference to the accompanying Figures. In the accompanying Figures, like reference numerals refer to similar features across multiple embodiments of the invention. It will be understood by those skilled in the art that while the Figures describe the present invention with reference to exemplary embodiments, the present invention is intended to be limited only by the claims appended hereto. Moreover, it will be understood by those skilled in the art that various features of the invention may be described with reference to one or more embodiments and are intended to be applicable to each embodiment described in the specification and within the scope of the appended claims.

DESCRIPTION OF THE FIGURES

FIG. 2A is a fragmentary cross-sectional view of a section of the inventive rapid exchange vena cava filter catheter illustrating a rapid exchange guide wire port and a medial contrast port.

FIG. 2B is a fragmentary top view taken from direction of arrow 2B in FIG. 2A and is a section of the inventive rapid exchange vena cava filter catheter illustrating a rapid exchange guide wire port and a medial contrast port.

FIG. 5 is a perspective view of another embodiment of a rapid exchange guide wire port of the inventive rapid exchange vena cava filter catheter.

FIG. 6 is a cross-sectional view taken along line 6-6 of FIG. 5.

FIGS. 7A-7C are sequential perspective views depicting a method of assembling the rapid exchange guidewire port depicted in FIG. 5.

FIG. 9A is a side elevational view of the proximal hub of the inventive rapid exchange vena cava filter catheter in accordance with the present invention.

FIG. 9B is a top plan view of the proximal hub of the inventive rapid exchange vena cava filter catheter in accordance with the present invention.

FIG. 10 is a side elevational view of a vena cava filter member of the inventive rapid exchange vena cava filter catheter in accordance with the present invention.

FIG. 10A is a cross-sectional view taken along line 10A-10A of FIG. 10.

FIG. 10B is a cross-sectional view taken along line 10B-10B of FIG. 10.

FIG. 11 is a side elevational view of another embodiment of the vena cava filter member of the inventive rapid exchange vena cava filter catheter in accordance with the present invention.

FIG. 12 is a cross-sectional view taken along line 12-12 of FIG. 11.

FIG. 13 is a cross-sectional view taken along line 13-13 of FIG. 11.

DETAILED DESCRIPTION OF THE INVENTION

Figure 1:
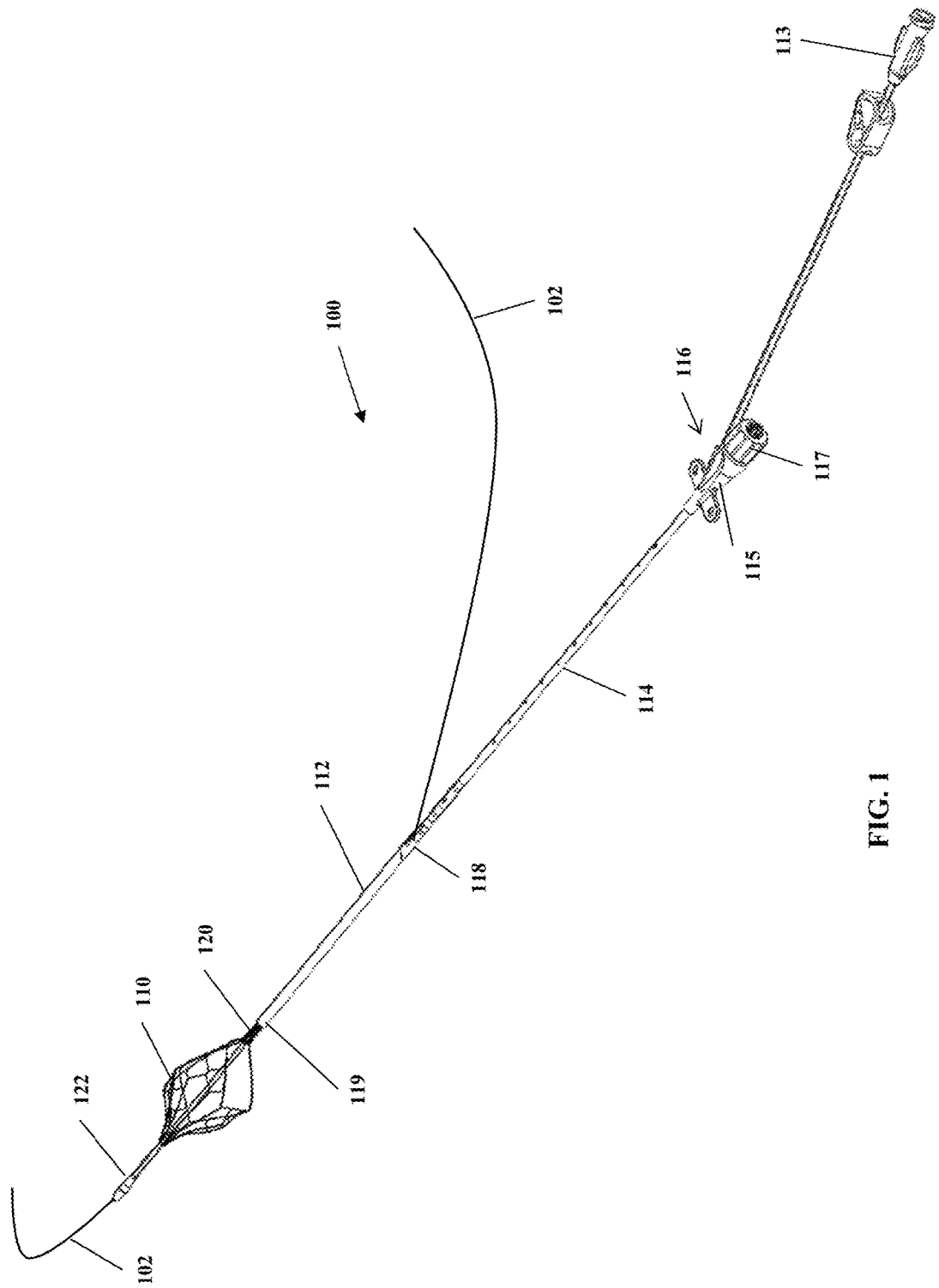
FIG. 1 is a perspective view of a rapid exchange vena cava filter catheter in accordance with the present invention.

In accordance with the present invention, there is provided a rapid exchange vena cava filter catheter 100. Rapid exchange vena cava filter catheter 100 includes generally a vena cava filter member 110 that is coupled to an elongate member 120, such as an elongate wire 120. The vena cava filter member 110 is more fully described with reference to commonly owned U.S. Pat. Nos. 8,613,753, 8,668,712, 8,771,226, 8,777,977, 8,777,981 and/or 8,808,323, each of which is hereby incorporated by reference. Briefly, the vena cava filter member 110 is formed of a plurality of strut members forming first and second conical sections of the filter member 110. The first and second conical sections define proximal and distal ends of the filter member 110. Each of the first and second conical sections have a base and an apex, with the apices of each of the first and second conical sections forming one of the proximal and distal ends of the filter member 110, with the base of each conical section being positioned intermediate the proximal and distal ends of the filter member 110.

The rapid exchange vena cava filter catheter 100 also includes a catheter sheath member formed from a proximal catheter sheath 114 and a distal catheter sheath 112. At a proximal end of the proximal catheter sheath 114 is provided a proximal hub 116. The catheter sheath member has a central longitudinal lumen that extends from and is in fluid flow communication with the proximal hub. The central longitudinal lumen of the catheter sheath extends to a distal end 119 of the catheter sheath member and terminates at a distal opening in the distal catheter sheath 112. An elongate wire 120 passes through the catheter sheath member and extends at its proximal end from the proximal hub and is coupled near its distal end to the filter member 110. In another embodiment, the elongate wire 120 may be a tube, including, for example a single lumen or a multi-lumen tube to provide an additional lumen the rapid exchange or dual lumen design configurations. As used herein, the term elongate wire 120 is intended to encompass a wire or a tube. The elongate wire 120 is capable of being longitudinally translated within and through the catheter sheath member in order to push the filter member 110 out of the distal end 119 of the catheter sheath member and also retract the filter member 110 back into the distal end 119 of the catheter sheath member. An atraumatic tip 122 is provided at a very distal end of the elongate wire 120 to facilitate navigation of the rapid exchange vena cava filter catheter 100 through the vasculature or other anatomic passageway.

A rapid exchange guide wire port 118 is provided in the catheter sheath member and is positioned generally at the transition between the proximal catheter sheath 114 and the distal catheter sheath 112. The rapid exchange guide wire port 118 permits a guide wire 102 to exit from the rapid exchange guide wire port 118.

Each of the first and second conical sections of the filter member 110 are asymmetrical relative to each other. For example, a length of the first conical section will be either greater than or less than a length of the second conical section. Additionally, the number and configuration of struts forming the first conical section will be different than the number and configuration of struts forming the second conical section of the filter member 110. It has been found advantageous to configure the filter member 110 such that whichever of the first and second conical sections are oriented toward the direction of fluid flow within the body structure, i.e., retrograde relative to the fluid flow, that section have a lower number of struts and interstitial openings between struts in that section be of a relatively larger open surface area relative to the other section that is oriented away from the direction of fluid flow within the body structure, i.e., antegrade relative to the fluid flow. For example, when delivered infra-renal within the inferior vena cava by a femoral approach, blood flow is in a cephalic direction, i.e., toward the patient's head, thus, the conical section of the filter member 110 that tapers toward an apex that is retrograde to the blood flow within the inferior vena cava, i.e., pointed caudal relative to the patient, will be configured to have interstitial spaces relatively larger than the conical section of the filter member 110 that tapers toward and apex that is antegrade to the blood flow with in the inferior vena cava, i.e., pointed cephalic relative to the patient, which will be configured to have interstitial spaces that are relatively smaller in order to capture thrombus. FIGS. 10 and 11, described in greater detail hereinafter, illustrate this described configuration and orientation of the filter member 110.

Figure 2C:
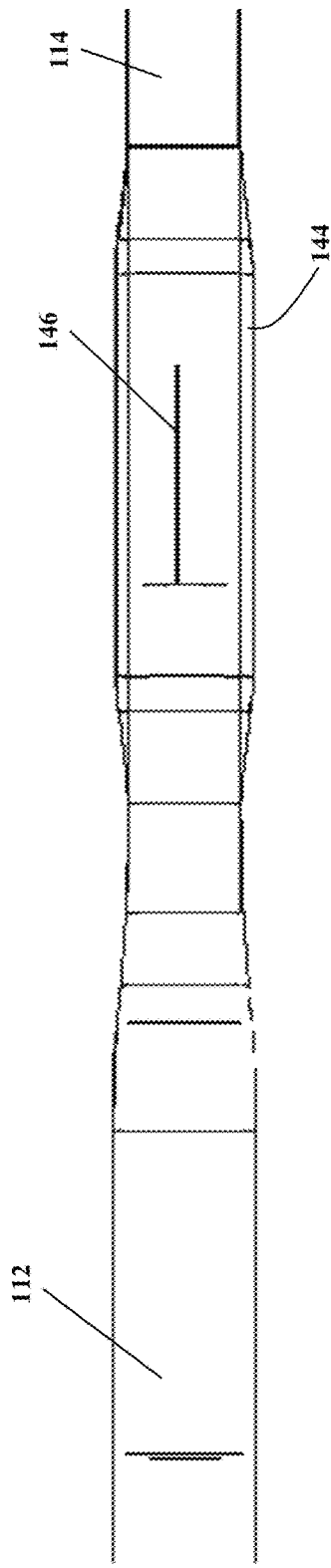
FIG. 2C is a fragmentary top view taken from direction of arrow 2C in FIG. 2A and is a section of the inventive rapid exchange vena cava filter catheter illustrating a rapid exchange guide wire port and a medial contrast port.

The rapid exchange guide wire port 118 is depicted in FIGS. 2A-2B in greater detail. As discussed above, the rapid exchange guide wire port 118 consists of a large opening in the side wall of the rapid exchange catheter member. It will be understood that port 118 may be positioned at any longitudinal position along the length of the rapid exchange catheter member. However, for purposes of illustration and in accordance with one aspect of the present invention, rapid exchange guide wire port 118 is positioned at the transition between the proximal catheter sheath member 114 and the distal catheter sheath member 112. Proximal catheter sheath member 114 has a transverse diameter D2 that is smaller than a transverse diameter D1 of the distal catheter sheath member 112. Alternatively, the catheter could be configured to have a substantially uniform diametric profile along the entire longitudinal length of the device depending on geometry required. The port 118 is positioned at the diametric transition between the proximal catheter sheath member 114 and the distal catheter sheath member 112.

Because of its relatively large open surface area necessitated by its function, the guide wire port 118 must be sealed to prevent undesired fluid flow out of or into the port 118. In order to seal port 118, a resilient seal 130 is provided within the lumen 113 of the distal catheter sheath member 114 that seats against a luminal wall surface surrounding the rapid exchange guide wire port 118. Resilient seal 130 is deformable in order to accommodate passage of a guide wire past the seal and through the port 118 opening, while still providing a substantially fluid tight seal to reduce or prevent fluids from passing through the port 118 opening. Resilient seal 130 preferably has a tapered section 134 that projects distally toward the vena cava filter member 110, yet permits fluid to flow from lumen 113 in the distal catheter sheath member 112 past or through the resilient seal 130 and into a second lumen 135 in communication therewith within the proximal catheter sheath member 114. In accordance with one aspect of the invention, resilient seal 130 consists of a generally tubular member that has a proximal end 132 which is generally cylindrical and capable of being joined to the proximal catheter sheath member 114, and a distal end 134 that has a generally tapered frustroconical shape, tapering distally and ending in a distal seal opening 138. Alternatively, the resilient seal 130 may have a generally tubular shape with one wall surface of the seal 130 forming a diametrically enlarged bulge 131 toward an intermediate aspect of the seal 130 which then tapers toward the distal end 134 and opens at distal seal opening 138. The diametrically enlarged bulge 131 seats against the luminal wall surface perimeter rapid exchange guide wire port 118 to seal port 118.

The resilient seal 130 has a seal lumen 135 that is in fluid communication at it proximal end 132 with the lumen 115 of the proximal catheter sheath member 114 and at its distal end 134, distal seal opening 138 is in fluid communication with lumen 113 of the distal catheter sheath member 112. In this manner, fluid introduced into proximal lumen 115 will pass through the resilient seal lumen 135 and into the distal lumen 113 of the distal catheter sheath member 112, without exiting the rapid exchange guide wire port 118.

FIGS. 5-6 illustrate an alternative embodiment of a resilient seal 200 and FIGS. 7A-7C represent a manner in which resilient seal 200 is disposed within the rapid exchange vena cava filter catheter 100. In accordance with the alternative embodiment of resilient seal 200, there is provided a resilient seal member 210 having a generally tubular cylindrical shape having a seal lumen 235 that passes through the resilient seal member 210 and opens at each end thereof. A proximal end 214 of the resilient seal member 210 is configured with an outer diameter sized to be inserted within and be coupled to an inner diameter of the proximal catheter sheath member 114. Thus, as depicted in FIGS. 7A and 7B, a proximal end 214 of the resilient seal member 210 is engaged within the distal end of lumen 115 of the proximal catheter sheath member 114. The proximal end 214 of the resilient seal member 210 may be joined to the proximal catheter sheath member 114 by any suitable method of creating just coupling, including, without limitation, reflow, thermal welding, ultrasonic welding, adhesive, interference or such other means for joining two components of a catheter device as are known in the art. Once the resilient seal 210 is joined to the proximal catheter sheath member 114, the distal catheter sheath member 112 may be engaged over the resilient seal 210, such that the guide wire port 118 is positioned over a portion of the resilient seal 210, and the distal catheter sheath member 112 and the proximal catheter sheath member 114 are joined by any suitable method of creating just coupling, including, without limitation, reflow, thermal welding, ultrasonic welding, adhesive, interference or such other means for joining two components of a catheter device as are known in the art.

A distal end 216 of the resilient seal member 210 has a beveled wall surface 212 that tapers distally toward the vena cava filter member 110 forming a guide wire ramp. In this manner, as the vena cava filter catheter 100 is passed over a guide wire 102, the guide wire 102 passes through distal lumen 113 of the distal catheter sheath member 112, and will be deflected by the beveled wall surface 212 that forms a ramp, the resilient seal 210 will deform to guide the guide wire 102 toward and out the rapid exchange guide wire port 118. In another embodiment, the guide wire ramp may be configured to facilitate guidance of the wire through the rapid exchange pathway, such as, for example, by forming a bevel or concave profile of the guide wire ramp.

Figure 3B:
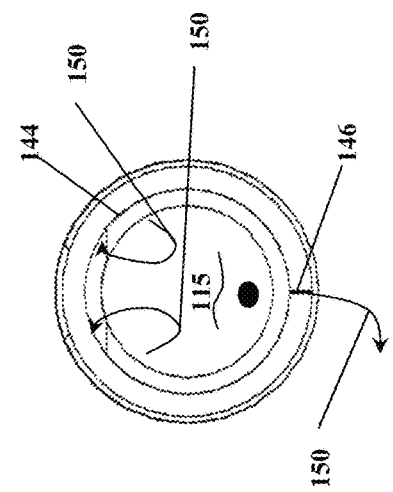
FIG. 3B is a transverse cross-sectional view taken along line 3B-3B of FIG. 3A.
Figure 3A:
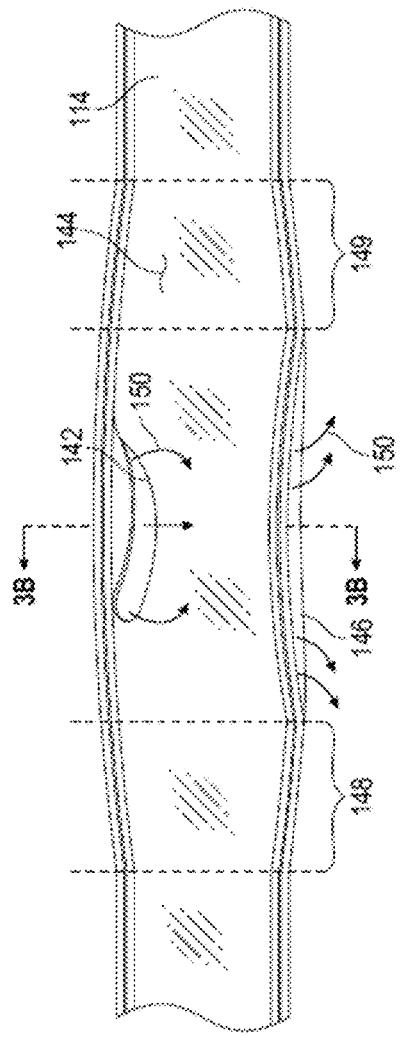
FIG. 3A is a side elevational view of a medial contrast port in accordance with the present invention.

The elongate wire 120 traverses the distal lumen 113 of the distal catheter sheath member 112, the seal lumen 235 and the proximal lumen 115 of the proximal catheter sheath member 114. While not shown in FIG. 5 or 6, the resilient seal member 210 may also optionally be employed in conjunction with the contrast port opening 142, sleeve 144 and contrast fluid outlet opening 146 as depicted in and described above with reference to FIGS. 2-3B. Moreover, while not shown in FIG. 5 or 6, the resilient seal member 210 may also optionally be employed in conjunction with the flow restrictor member 160 as depicted in and described above with reference to FIG. 2. Similarly, while not shown in FIG. 5 or 6, the resilient seal member 210 may also optionally be employed in conjunction with all of the contrast port opening 142, sleeve 210, contrast fluid outlet opening 146, and flow restrictor 160, as depicted in and described above with reference to FIGS. 2-3B.

Optionally, a contrast port 142 is provided in the rapid exchange vena cava filter catheter 100. Contrast port 142 may be disposed in a wall of the proximal catheter sheath member 114 and communicate with the lumen 115 of the proximal catheter member 114. It has been found desirable to position the contrast port 142 sufficiently proximal the filter member 110 so that adequate dispersion of a contrast medium will occur at the position of the filter member 110 for visualization of the filter 110 and its placement, or for visualization of the region proximal to the filter member. In accordance with the exemplary embodiment of the invention depicted in FIG. 2, the contrast port 142 is positioned proximal the rapid exchange guide wire port 118 and near a distal end 140 of the proximal catheter sheath member 114.

A flow restrictor member 160 having a restrictor lumen 162 may optionally be provided and interposed intermediate the contrast port 142 and the rapid exchange guide wire port 118. The restrictor lumen 162 is of a smaller diameter relative to the proximal lumen 115 of the proximal catheter sheath member 114 and is also smaller in diameter relative to the distal lumen 113 of the distal catheter sheath member 112. In this manner, flow restrictor member 160 permits regulation of pressures at which contrast medium is either emitted from contrast port 142 or pressures at which fluids, including contrast medium, flow through the restrictor lumen 162, through the resilient port seal 130 and through the distal lumen 113 of the distal catheter sheath member 112, exiting the rapid exchange vena cava filter catheter 100 at its distal end 119. It will be appreciated that at higher injection pressures, fluids, such as contrast medium, will encounter a back pressure exerted by the flow restrictor member 160 and will flow primarily out of the contrast port 142, with a secondary flow passing through restrictor lumen 162 and into the distal section of the catheter 100. At lower injection pressures, fluid will primarily flow distally through the restrictor lumen 160 and into the distal section of the catheter 100. It will be understood by those skilled in the art that the relative diameter and length of the restrictor lumen 160 relative to the diameter of the proximal lumen 115 and distal lumen 113 will determine the pressure above which the primary fluid flow will exit the contrast port 142.

Contrast port 142 may have an opening size dimensioned to regulate the outflow of contrast medium there through. However, in order to facilitate dispersion of the contrast medium in the blood flow, it has been found desirable to sheath the contrast port 118 with a sleeve 144 that circumferentially covers the proximal catheter sheath member 114 and covers the contrast port, while allowing a fluid flow channel 150 between an inner surface of the sleeve 144 and the outer surface of the proximal catheter sheath member 114. A contrast fluid outlet opening 146 is provided in the sleeve 144 and is spaced apart from the contrast port 142. One example is to position the contrast fluid outlet opening 146 180 degrees opposite from the contrast port 142 about the circumferential axis of the catheter sheath member 114. This position allows for the contrast medium to flow bidirectionally about the entire circumference of the catheter sheath member 114. Where the contrast fluid outlet opening 146 is formed as a slot oriented parallel to the longitudinal axis of the catheter sheath member 114, the contrast medium will flow out of the contrast fluid outlet opening 146 in a substantially laminar flow. The contrast fluid outlet opening 146 may be a single or plural circumferentially oriented slots, helical slots, longitudinally oriented slots, circular openings, polygonal openings, or other shaped openings as are appropriate to provide for dispersion of a contrast medium as it is released from the contrast port 142.

The sleeve 144 is preferably joined to the vena cava filter catheter 100 at proximal and distal aspects of the sleeve 144, leaving the fluid flow channel 150 in an unjoined intermediate aspect of the sleeve 144 that overlays the contrast port 142 and is in fluid communication with the contrast fluid outlet opening 146.

Figure 4:
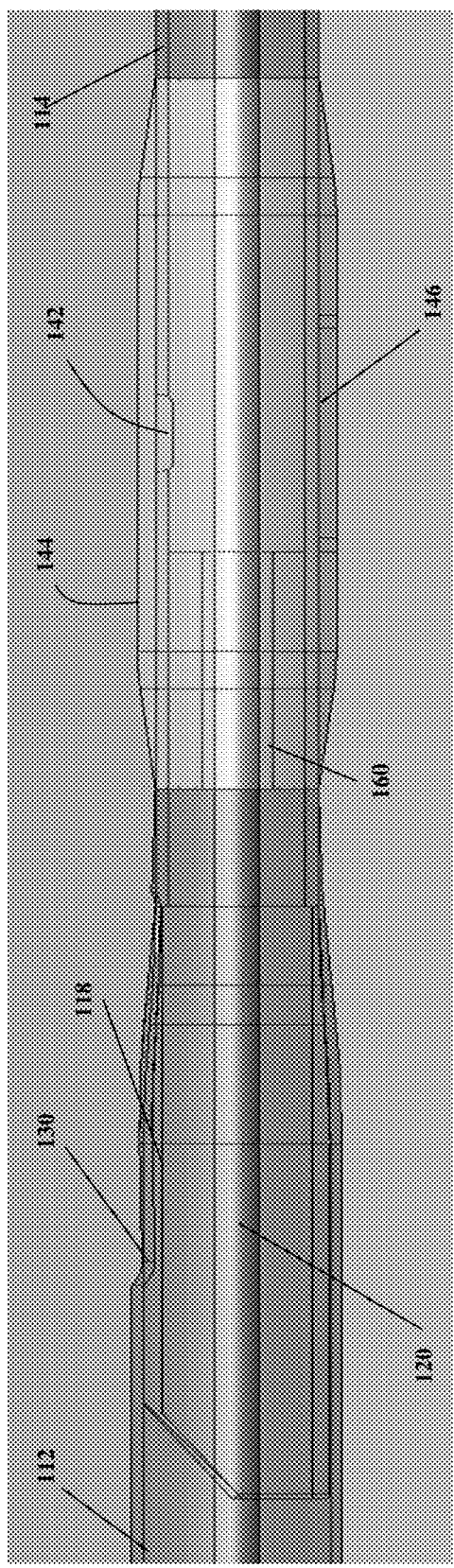
FIG. 4 is a side view of a section of the inventive rapid exchange vena cava filter catheter with the sheath shown in phantom illustrating the rapid exchange guide wire port, the medial contrast port and an in-line flow restrictor insert within a lumen of the inventive catheter.
Figure 8A:
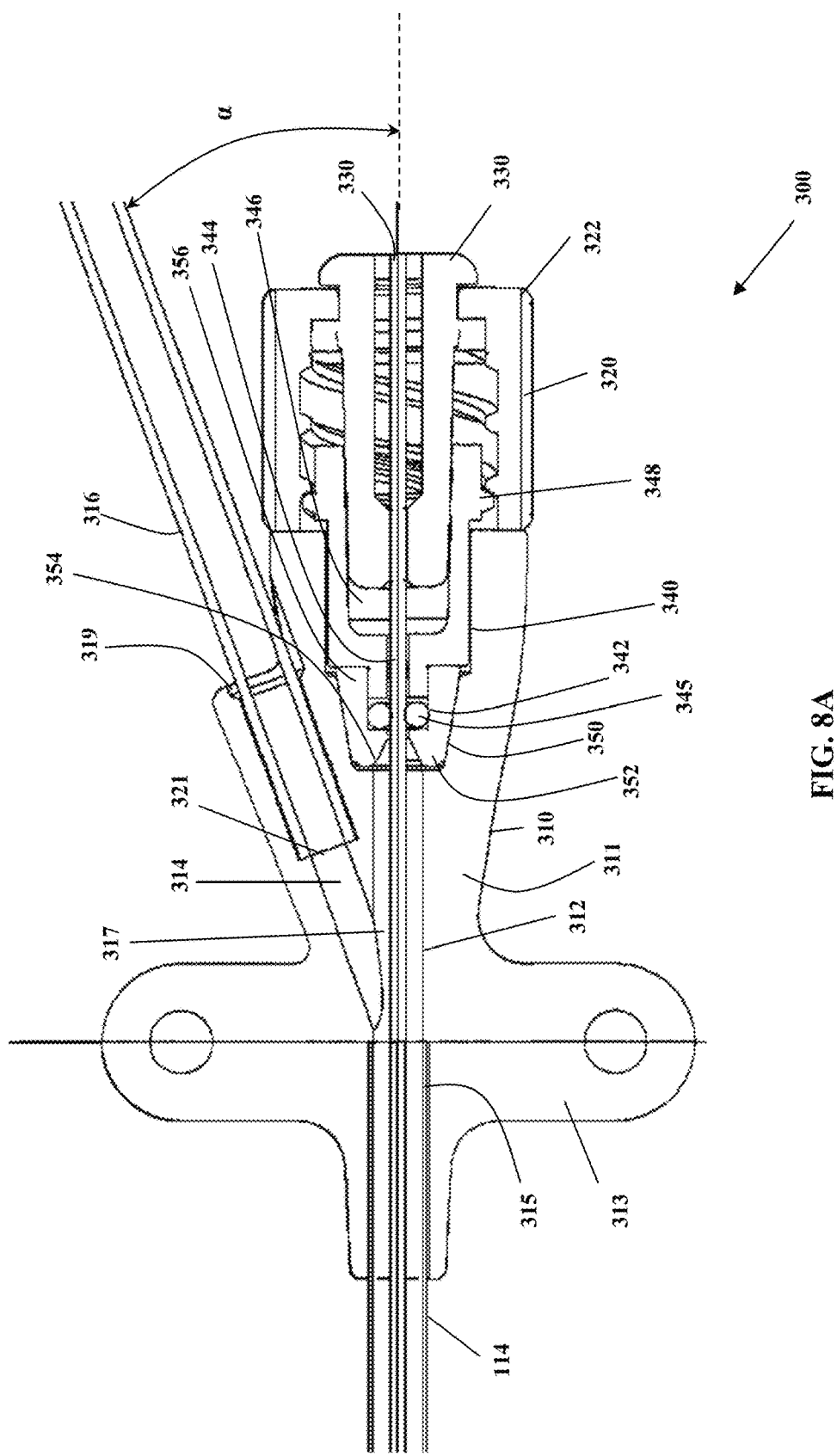
FIG. 8A is a top elevational fragmentary view of a proximal hub of the inventive rapid exchange vena cava filter in accordance with the present invention.
Figure 8B:
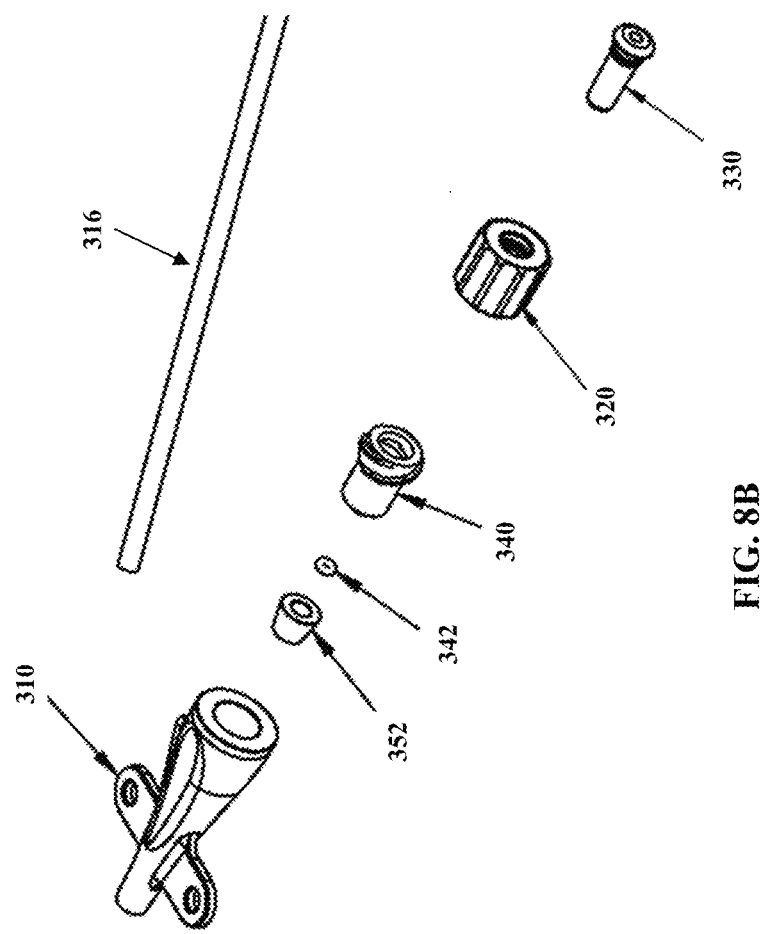
FIG. 8B is an exploded perspective view of the proximal hub of the rapid exchange vena cava filter in accordance with the present invention.

As illustrated in FIGS. 4 and 6, the elongate wire 120 traverses the proximal lumen 115 of the proximal catheter sheath member 114, passes through the flow restrictor lumen 162, if the flow restrictor member 160 is present, through the lumen 135 of the resilient seal 130 and then into the distal lumen 113 of the distal catheter sheath member 115. As noted above, the proximal end of vena cava filter member 110 is coupled to the distal end of the elongate wire 120.

Turning now to FIGS. 8A to 9C, a proximal hub 300 in accordance with the present invention is illustrated. The proximal hub 300 forms the proximal end of the rapid exchange vena cava catheter 100 and is the proximal terminus of the proximal catheter sheath member 114 and the elongate wire 120. The proximal hub 300 also provides fluid access for fluid injection into the proximal lumen 115 of the proximal catheter sheath member 114.

The proximal hub 300 includes first section 310 and a second section 320 that cooperate with each other. The first section 310, which is preferably a distal section of the proximal hub 300, is formed of a housing 311 having a first channel 312 and a second channel 314. First channel 312 has a receiving section 315 in a distal portion of the first channel 312 and a proximal section 317. A proximal end of the proximal catheter sheath member 114 engages and seats within the receiving section 315 of the first channel 312 and is in fluid flow communication with the proximal section 317. The proximal lumen 115 of the proximal catheter sheath member 114 is in fluid flow communication with the proximal section 317 of the first channel 312. The second channel 314 has a proximal receiving section 319 and a distal section 321. An extension line 316 engages and seats within the proximal receiving section 319 and is in fluid flow communication with the distal section 321 of the second channel 314. Distal section 321 of the second channel 314 joins in fluid flow communication with the distal section 317 of the first channel 312.

It has been found desirable that the first channel 312 be co-axial with a central longitudinal axis L of the proximal hub 300 and that the second channel 314 be angularly displaced from the central longitudinal axis L by an angle α. Angle α is preferably greater than 0 and less than or equal to 90 degrees, preferably between 15 and 45 degrees from the central longitudinal axis L.

The first housing 310 further includes a seating recess 350 that accommodates a hemostatic seal seating member 352 therein. Seating recess 350 is co-axial with the central longitudinal axis L and has a bore 354 in fluid communication with the proximal section 317 of the first channel 312. Seating recess 350 has a generally annular shape and has a proximal receiving recess 356 in a proximal aspect of the seating recess 350. Bore 354 tapers proximally and opens to the proximal receiving recess 356.

There is also provided a hemostatic sealing member 340 that has a distal projection 342 and a sealing member 345 interfacing between the distal projection 342 and the proximal receiving recess 356 of the seating recess 350 in the first housing 310. The hemostatic sealing member 340 further has a bore 344 passing through the hemostatic sealing member 340 and through the distal projection 242 that communicates with bore 354 in the seating recess. Finally, hemostatic sealing member 340 further includes an engagement section 348 having enlarged receiving bore 346 in a proximal aspect of the hemostatic sealing member 340 that communicates with the bore 344.

Finally, the first section 310 includes at least one, preferably two, apertures 311 for securing the proximal hub 300 to the patient. In the illustrated embodiment in FIGS. 8A-9C, apertures 311 are present in suture wings that project outwardly from the first section 310.

The second section 320 removably engages with the first section 310, such as by a threaded connection or a luer-type connection. Second section 320 is rotatably connected with a distal end of the elongate wire 120 (not shown in FIG. 8A), such as by a swage fitting. Second section 320 includes a rotatable cap housing 322 that removably couples to the first section 310, such as by engagement and disengagement with the engagement section 348 of the hemostatic sealing member 340. The distal end of the elongate wire 120 is connected within a wire bore 332 in a connecting fitting 330. Connecting fitting 330 is rotatably coupled to the rotatable cap housing 322, such that rotational movement of the rotatable cap housing 322 does not translate rotational forces to the connecting fitting 330 or to the elongate wire 120, but rather permits rotational coupling and decoupling of the rotatable cap housing 322 from the first section 310 of the proximal hub 300 and then allows for longitudinal translation of the elongate wire 120, the rotatable cap housing 322 and the connecting fitting 330 relative to the first section 310. It will be understood that this longitudinal translation of the elongate wire 120 serves to push the vena cava filter member 110 coupled to the distal end of the elongate wire 120 out of the distal end 119 of the distal catheter sheath member 112 and also to retrieve the vena cava filter member 110 within the distal end 119 of the distal catheter sheath member 112.

In accordance with one embodiment of the proximal hub 300, the first section 310 and the seating recess 350 may optionally be fabricated of pliant or resilient materials. In this embodiment, proximal hub 300 may have resilient or pliant opposing first and second surfaces 315, 317, respectively. By fabricating the seating recess 350 of a pliant or resilient material, bore 354 may be dimensioned to bear against the elongate wire 120 and exert a pressure that creates drag when the elongate wire 120 is translated through the bore 354. Deformation of the seating recess 350 will deform the bore 354 and release some of the pressure bearing against the elongate wire 120. In use, the medical practitioner may depress first and second surfaces 315, 317 to deform the first section 310 and the seating recess 350 therein, thereby deforming the bore 354 surrounding the elongate wire 120 passing there through and releasing pressure by the bore 354 bearing against the elongate wire 120 to allow for smoother longitudinal translation of the elongate wire 120 through the proximal hub 300.

One embodiment of the filter member 110 is illustrated in its diametrically expanded configuration in FIG. 10. In this embodiment, filter member 110 consists of a plurality of strut members 12 arranged to form a first generally conical end 18 and a second generally conical end 20 of the filter member 110. The plurality of strut members 12 define wall surfaces of the filter member 110 and delineate a first space 22 and a second space 24 within the filter member 110 for capturing thrombus sequestered from the circulating blood flow by at least some of the plurality of strut members 12.

In addition to forming a first generally conical end 18 and a second generally conical end 20, optionally, some of the plurality of strut members 12 may be arranged to form an intermediate section 16 of the second generally conical end 20 of the filter member 110. The intermediate section 16 is characterized by having interstitial openings 19 that are smaller relative to the interstitial openings 15 of the first generally conical end 18 or the interstitial openings 13 of the second generally conical end 20.

The first generally conical end 18 may form either the proximal or the distal end of the filter member 110 depending upon the orientation of the filter on the catheter and the anatomical approach for which the rapid exchange vena cava filter catheter 100 is intended, e.g., femoral or jugular. In forming the first generally conical end 18, a plurality of first strut members 62, for example three, are coupled at their proximal end to the proximal end 18 of filter member 110 and each extends distally relative to the longitudinal axis of the rapid exchange vena cava catheter 100. Each of the first strut members 62 is an elongate member that projects away from the central longitudinal axis of the catheter 100 and terminates in a distal end section 63 that defines a base of the first generally conical end 18. A plurality of second strut members 64 extend from a distal end of the second generally conical end and extend proximally form a distal end of are coupled at their distal end to the distal end 20 of filter member 110 and each extends proximally relative to the longitudinal axis of the catheter 100. A plurality of third strut members 66 form the intermediate section 26, if present, and at least some of the plurality of third strut members 66 are joined at their distal ends to a proximal end of at least some of the plurality of second strut members 64, and at least some of the plurality of third strut members 66 are joined at their proximal ends a distal end of at least some of the plurality of first strut members 62. A hoop member 70, which may be formed from some of the plurality of third strut members 66, extends circumferentially to define a circumferential axis of the filter member 110 and has a series of continuous undulations defining a series of peaks 75 and valleys 77 about the circumference of filter member 110. Each of the plurality of first strut members 62, the plurality of second strut members 64 and the plurality of third strut members 66 are coupled to the hoop member 70 at different points about its circumferential axis and intermediate the proximal end 18 and the distal end 20 of the filter member 110.

The plurality of first strut members 62 are preferably evenly offset from each other. For example, where three first strut members 62 are employed, each will be offset by approximately 120 degrees about the circumference of the filter member 110. The plurality of second strut members 64 are also preferably evenly offset from each other. Thus, for example, if twelve second strut members are employed, each will be offset by approximately thirty degrees about the circumference of the filter member 110.

It will be understood that each of the plurality of first strut members 62, plurality of second strut members 64, plurality of third strut members 66 and the hoop member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

FIGS. 10-10B and 11-13 illustrate two alternate attachments of the filter member 410, 510 to the elongate wire 120. In each embodiment, the filter member 410, 510 is attached to a distal end of the elongate wire 210 by means of an attachment tube 40. A filter attachment member 30, such as that described in U.S. Pat. No. 8,808,323, which is hereby incorporated by reference, is employed to couple the filter member 410, 510 to the attachment tube 40.

As illustrated in FIGS. 10-10C, attachment tube 40 has a guide wire lumen 27 that extends from a distal end of the attachment tube 40 and passes through the atraumatic tip 122. Guide wire lumen 27 terminates proximal to the filter attachment member 30 in the guide wire port 118. A second lumen 29 is provided in the attachment tube 40 that extends and opens to a proximal end of the attachment tube 40. The distal end of the elongate wire 120 is received within the second lumen 29 and the elongate wire 120 is secured therein. The guide wire port 118 aligns with a port 118*a* disposed on the distal catheter sheath 114 when the filter member 110 is in contracted state.

Like with filter 410, and as illustrated in FIGS. 11-13, filter 510 is also coupled to a filter attachment tube 40. In this embodiment, however, filter attachment tube 40 has a guide wire lumen that passes along an entire longitudinal length of the filter attachment tube 40 and opens distally at the atraumatic tip 122 and proximally at the proximal end of the filter attachment tube 40. Like with filter 410, a second lumen 29 is provided in the attachment tube 40 that extends and opens to a proximal end of the attachment tube 40. The distal end of the elongate wire 120 is received within the second lumen 29 and the elongate wire 120 is secured therein.

It is contemplated that the elongate wire 120 may be made of any suitably biocompatible metal, such as nickel-titanium alloy, chromium-molybdenum alloy, stainless steel or the like. The elongate wire 120 may optionally be reinforced with a winding of another metal wire or may be coated with a polymer and/or a bioactive agent, such as an antithrombotic agent. It is further contemplated that the proximal and distal catheter sheaths 114, 112, may be made of any suitably biocompatible polymer, such as polyurethane, polytetrafluoroethylene, polyether block amide (PEBAX®, Arkema, Paris, France), and may also optionally be coated or covered with another polymer and/or a bioactive agent, such as an antithrombotic agent. It is also contemplated that the vena cava filter member 110, 410, 510 may be made of any suitably biocompatible metal or polymer, as are known in the art. Finally, the attachment tube 40 may be made of any suitably biocompatible metal, such as nickel-titanium alloy or polyether block amide (PEBAX®, Arkema, Paris, France).

It will be understood by those skilled in the art that the foregoing description of the inventive rapid exchange vena cava filter catheter is made with reference to exemplary embodiments only. Such exemplary embodiments are not intended to be, nor should be construed to be limiting of the scope of the invention, which is defined solely by the claims appended hereto.

What is claimed is:

1. A vena cava filter catheter system, comprising:
a first catheter member having a first lumen passing longitudinally through the first catheter member and in fluid flow communication with a proximal end thereof and a distal end thereof, the first catheter member further comprising a second opening in a wall surface of the first catheter member, the second opening being positioned proximal to a distal end of the first catheter member, wherein the second opening is configured to permit a contrast agent to be released therefrom;
a second catheter member having a second lumen passing longitudinally through the first catheter member, a proximal end and a distal end thereof, the second catheter member having a first opening passing through a wall thereof near a proximal end of the second catheter member, the proximal end of the second catheter member being joined to the distal end of the first catheter member, wherein the first opening in the second catheter member further comprises a rapid exchange guide wire port and the rapid exchange guide wire port comprises an elongate opening having a generally larger distal opening and a generally smaller proximal opening; wherein the generally larger distal opening has a circumferential extent relative to the circumference of the second catheter member that is greater than the circumferential extent of the generally smaller proximal opening;
a resilient seal member disposed within the second lumen of the second catheter member and coupled to the proximal end of the second catheter member, the resilient seal member covering the first opening from within the second lumen and being deformable so as to be capable of accepting a guide wire to pass through the first opening and into the second lumen, the resilient seal member further comprises a generally tubular member having a distally tapering end; wherein the resilient seal member further comprises a proximal section having a diameter smaller than an adjacent more distal section;
an elongate wire passing longitudinally within the first lumen from a proximal end of the first catheter member and within the second lumen of the second catheter member;
a sleeve member having a third opening, the sleeve member being circumferentially joined about the distal end of the first catheter member such that a proximal and distal end of the sleeve member are coupled to the first catheter member, leaving an uncoupled intermediate section of the sleeve member covering the second opening of the the first catheter member, the sleeve member having a fourth opening circumferentially spaced apart from the second opening in the first catheter member, such that a fluid flow path is formed between the fourth opening of the sleeve member, the uncoupled intermediate section and the third opening;
a flow restrictor member within one of the first lumen of the first catheter member or the second lumen of the second catheter member and positioned proximal to the first opening in the second catheter member, wherein the flow restrictor member further comprises a generally cylindrical member having a central bore, the central bore having a diameter less than a diameter of the first lumen of the first catheter member and less than a diameter of the second lumen of the second catheter member;
an expandable vena cava filter member fixedly coupled to a distal end of the elongate wire, the expandable vena cava filter member having a collapsed state when within the second lumen of the second catheter member and an expanded state when outside the second lumen of the second catheter member, the expandable vena cava filter member being released from and retrieved into the second lumen by longitudinal translation of the elongate wire relative to the first catheter member and the second catheter member; and
a proximal hub having at least two ports operably coupled to a proximal end of the first catheter member, a first of the at least two ports being in fluid flow communication with the first lumen of the first catheter member, and a second of the at least two ports accommodating the elongate wire passing there through such that the elongate wire is accessible from a proximal end of the second of the at least two ports of the proximal hub.

2. The vena cava filter system of claim 1, wherein the proximal section is joined within a distal section of the first lumen of the first catheter member; and wherein a circumferential portion of the distal section of the resilient seal member abuts a luminal aspect of and movably seals the first opening in the second catheter member.

3. The vena cava filter system of claim 2, wherein the distally tapering end of the resilient seal member forms a distal opening of the resilient seal member having a diameter relatively smaller than a diameter of a proximal opening of the proximal section of the resilient seal member; and wherein the distally tapering end of the resilient seal member forms a distal opening of the resilient seal member having a diameter substantially the same as a diameter of the rest of the distal section of the resilient seal member.

4. The vena cava filter system of claim 3, wherein the proximal hub further comprises a hemostasis seal in the second of the at least two ports accommodating the elongate wire; and wherein the hemostasis seal further comprises a resilient O-ring seal through which the elongate wire passes.

5. The vena cava filter system of claim 4, wherein the hemostasis seal further comprises a channel in the proximal hub through which the elongate wire passes and contacts walls of the channel to provide a hemostasis seal about the elongate wire; and wherein the proximal hub is at least partially made of a resilient material and the channel is configured to open upon deformation of the resilient material and release substantial contact between the walls of the channel and the elongate wire.

6. A vena cava filter catheter system, comprising:
a. A first catheter member having a first lumen passing longitudinally through the first catheter member and in fluid flow communication with a proximal end thereof and a distal end thereof, the first catheter member having a first and second opening passing through a wall of the first catheter member proximate the distal end of the first catheter member;
b. A second catheter member having a second lumen passing longitudinally through the first catheter member, a proximal end and a distal end thereof, the second catheter member having a third opening passing through a wall thereof near a proximal end of the second catheter member, the proximal end of the second catheter member being joined to the distal end of the first catheter member such that the juncture between the first catheter member and the second catheter member is positioned longitudinally between the first and second openings in the first catheter member and the third opening in the second catheter member, wherein the first opening and the second opening are configured to permit a contrast agent to be released therefrom and wherein the third opening in the second catheter member further comprises a rapid exchange guide wire port and the rapid exchange guide wire port comprises an elongate opening having a generally larger distal opening and a generally smaller proximal opening, the generally larger distal opening having a circumferential extent relative to the circumference of the second catheter member that is greater than the circumferential extent of the generally smaller proximal opening;

c. A sleeve member circumferentially joined about the distal end of the first catheter member such that a proximal and distal end of the sleeve member are coupled to the first catheter member, leaving an uncoupled intermediate section of the sleeve member covering the first opening, the sleeve member having a fourth opening circumferentially spaced apart from the first opening in the first catheter member, such that a fluid flow path is formed between the first opening, the uncoupled intermediate section and the fourth opening of the sleeve member;

d. A flow restrictor member disposed within one of the first lumen of the first catheter member or the second lumen of the second catheter member, the flow restrictor member being positioned intermediate the first opening and the third opening, wherein the flow restrictor member further comprises a generally cylindrical member having a central bore, the central bore having a diameter less than a diameter of the first lumen of the first catheter member and less than a diameter of the second lumen of the second catheter member;

e. A resilient seal member disposed within the second lumen of the second catheter member and coupled to the proximal end of the second catheter member, the resilient seal member covering the third opening from within the second lumen and being deformable so as to be capable of accepting a guide wire to pass through the third opening and into the second lumen, wherein the resilient seal member further comprises a generally tubular member having a distally tapering end and wherein the resilient seal member further comprises a proximal section having a diameter smaller than an adjacent more distal section;

f. An elongate wire passing longitudinally within the first lumen from a proximal end of the first catheter member and within the second lumen of the second catheter member;

g. An expandable vena cava filter member fixedly coupled to a distal end of the elongate wire, the expandable vena cava filter member having a collapsed state when within the second lumen of the second catheter member and an expanded state when outside the second lumen of the second catheter member, the expandable vena cava filter member being released from and retrieved into the second lumen by longitudinal translation of the elongate wire relative to the first catheter member and the second catheter member; and h. A proximal hub having at least two ports operably coupled to a proximal end of the first catheter member, a first of the at least two ports being in fluid flow communication with the first lumen of the first catheter member, and a second of the at least two ports accommodating the elongate wire passing there through such that the elongate wire is accessible from a proximal end of the second of the at least two ports of the proximal hub.

7. The vena cava filter system of claim 6, wherein the proximal section of the resilient seal member is joined within a distal section of the first lumen of the first catheter member; and wherein a circumferential portion of the distal section of the resilient seal member abuts a luminal aspect of and movably seals the third opening in the second catheter member.

8. The vena cava filter system of claim 7, wherein the distally tapering end of the resilient seal member forms a distal opening of the resilient seal member having a diameter relatively smaller than a diameter of a proximal opening of the proximal section of the resilient seal member.

9. The vena cava filter system of claim 8, wherein the proximal hub further comprises a hemostasis seal in the second of the at least two ports accommodating the elongate wire; and wherein the hemostasis seal further comprises a resilient O-ring seal through which the elongate wire passes.

10. The vena cava filter system of claim 9, wherein the hemostasis seal further comprises a channel in the proximal hub through which the elongate wire passes and contacts walls of the channel to provide a hemostasis seal about the elongate wire; and wherein the proximal hub is at least partially made of a resilient material and the channel is configured to open upon deformation of the resilient material and release substantial contact between the walls of the channel and the elongate wire.

* * * * *